United States Patent [19]

Baldwin et al.

[11] Patent Number: 5,428,157
[45] Date of Patent: Jun. 27, 1995

[54] 3-ACYLAMINOBENZODIAZEPINES

[75] Inventors: John J. Baldwin, Gwynedd Valley; David A. Claremon, Maple Glen; Jason M. Elliott; Nigel Liverton, Harleysville; David C. Remy, North Wales; Harold G. Selnick, Ambler, all of Pa.

[73] Assignee: Merck & Co., Inc., Rahway, N.J.

[21] Appl. No.: 155,670

[22] Filed: Nov. 22, 1993

[51] Int. Cl.[6] .................. C07D 243/12; A61K 31/55
[52] U.S. Cl. ...................................... 540/509; 540/483
[58] Field of Search ................. 540/509, 483; 514/521

[56] References Cited

U.S. PATENT DOCUMENTS 4,820,834  4/1989  Evans et al. ............ 540/509
5,166,151 11/1992  Freidinger et al. ........ 540/509

FOREIGN PATENT DOCUMENTS

0514133A1 11/1992  European Pat. Off. ......... 540/509
0538945A1  4/1993  European Pat. Off. ......... 540/509
93/02078   2/1993  WIPO ....................... 540/509
93/07131   4/1993  WIPO ....................... 540/509
93/08176   4/1993  WIPO ....................... 540/509
93/17011   9/1993  WIPO ....................... 540/509
93/19063   9/1993  WIPO ....................... 540/509

*Primary Examiner*—Robert T. Bond
*Attorney, Agent, or Firm*—Sylvia A. Ayler; Francis P. Bigley; Mark R. Daniel

[57] ABSTRACT

3-Acylamino-5-Aminobenzo[1,5]diazepines are useful in the treatment of arrhythmia. The compounds have structural formulae:

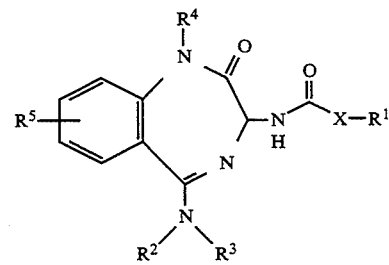

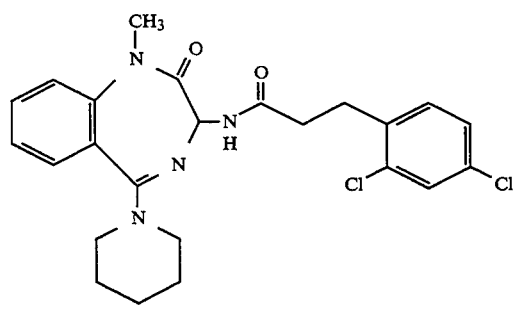

7 Claims, No Drawings

3-ACYLAMINOBENZODIAZEPINES

SUMMARY OF THE INVENTION

This invention is concerned with novel compounds represented by structural formula I.

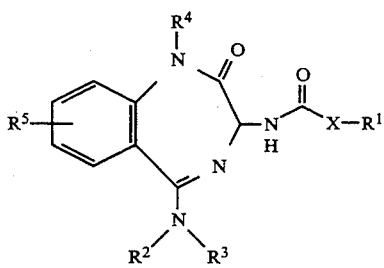

or a pharmaceutically acceptable salt thereof, which are useful as antiarrhythmic agents. The invention is also concerned with pharmaceutical formulations comprising one of the novel compounds as an active ingredient.

The invention is also, concerned with a method of treating arrhythmia by the administration of one of the novel compounds or formulation thereof to a patient in need of such treatment.

BACKGROUND OF THE INVENTION

Arrhythmias often occur as complications to cardiac diseases such as myocardial infarction and heart failure. In a serious case, arrhythmias give rise to a ventricular fibrillation and can cause sudden death.

Though various antiarrythmic agents are now available on the market, those, having both satisfactory effects and high safety, have not been obtained. For example, antiarrythmic agents of Class I according to the classification of Vaughan-Williams which cause a selective inhibition of the maximum velocity of the upstroke of the action potential (Vmax) are inadequate for preventing ventricular fibrillation. In addition, they have problems regarding safety, namely, they cause a depression of the myocardial contractility and have a tendency to induce arrythmias due to an inhibition of the impulse conduction. Beta-adrenoceptor blockers and calcium antagonists which belong to Class II and IV respectively, have a defect that their effects are either limited to a certain type of arrhythmia or are contraindicated because of their cardiac depressant properties in certain patients with cardiovascular disease. Their safety, however, is higher than that of the antiarrhythmic agents of Class I.

Antiarrythmic agents of Class III are drugs which cause a selective prolongation of the duration of the action potential without a significant depression of the Vmax. Drugs in this class are limited. Examples such as sotalol and amiodarone have been shown to possess Class III properties. Sotalol also possesses Class II effects which may cause cardiac depression and be contraindicated in certain susceptible patients. Also, amiodarone is severely limited by side effects. Drugs of this class are expected to be effective in preventing ventricular fibrillations. Pure Class III agents, by definition, are not considered to cause myocardial depression or an induction of arrhythmias due to the inhibition of the action potential conduction as seen with Class I antiarrhythmic agents.

DETAILED DESCRIPTION OF THE INVENTION

The novel compounds of this invention have structural formula I:

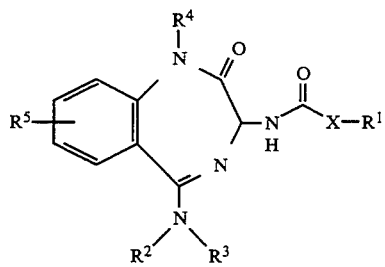

or a pharmaceutically acceptable salt thereof wherein:

X is $C_{1-4}$ alkylene, either straight or branched chain;

$R^1$ is
1) phenyl either unsubstituted or substituted with one or two substituents selected from chloro, trifluoromethyl, bromo, fluoro, $C_{1-3}$ alkoxy, nitro or iodo;
2) naphthyl, or
3) $C_{5-7}$ cycloalkyl, R2 and R3 are independently
1) $C_{1-3}$ alkyl, either straight or branched chain, and either unsubstituted or substituted with phenyl, or
2) $C_{3-7}$ cycloalkyl; or $R^2$ and $R^3$ taken together represent a $C_{4-7}$ methylene chain to form with the nitrogen to which they are attached a 5-8 membered azacycle;

$R^4$ is
1) $C_{1-4}$ alkyl,
2) phenyl or
3) benzyl; and

R5 is
1) hydrogen or
2) $C_{1-3}$ alkyl.

The pharmaceutically acceptable salts of the compounds of Formula I include the conventional non-toxic salts or the quaternary ammonium salts of the compounds of Formula I formed, e.g., from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glucolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the compounds of Formula I which contain a basic or acidic moiety by conventional chemical methods. Generally, the salts are prepared by reacting the free base or acid with stoichiometric amounts or with an excess of the desired salt-forming inorganic or organic acid or base in a suitable solvent or various combinations of solvents.

One embodiment of the novel compounds of this invention is that in which $R^2$ and $R^3$ are joined together to form a 5-8-membered heterocycle.

Representative of the compounds within this embodiment are those depicted in Table I.

TABLE I

| X | R¹ | R²—R³ | R⁴ |
|---|---|---|---|
| —CH₂— | 1-naphthyl | —(CH₂)₅— | n-propyl |
| —(CH₂)₂— | 2,4-diClPh | —(CH₂)₆— | methyl |
| —(CH₂)₂— | 4-CF₃Ph | —(CH₂)₆— | methyl |
| —(CH₂)₃— | cyclohexyl | —(CH₂)₆— | methyl |
| —(CH₂)₄— | Ph | —(CH₂)₆— | methyl |
| —CH₂— | 1-naphthyl | —(CH₂)₆— | n-propyl |
| —(CH₂)₃— | Ph | —(CH₂)₆— | methyl |
| —(CH₂)₂— | cyclohexyl | —(CH₂)₆— | methyl |
| —CH₂— | cyclohexyl | —(CH₂)₆— | methyl |

A second embodiment of the novel compounds of this invention is that wherein $R^2$ and $R^3$ are independently $C_{1-3}$ alkyl or $C_{3-7}$ cycloalkyl.

Representative of this embodiment are the compounds depicted in Table II.

TABLE II

| X | R¹ | R⁴ |
|---|---|---|
| —(CH₂)₂— | 4-CF₃Ph | —CH₃ |
| —(CH₂)₃— | cyclohexyl | —CH₃ |
| —(CH₂)₂— | 2,4-diClPh | —CH₃ |
| —(CH₂)₂— | 2,4-diClPh | n-propyl |
| —(CH₂)₂— | cyclohexyl | n-propyl |
| —CH₂— | cyclohexyl | n-propyl |
| —(CH₂)₂— | Ph | —CH₃ |
| —CH₂— | cyclohexyl | —CH₃ |
| —(CH₂)₃— | Ph | —CH₃ |
| —(CH₂)₂— | cyclohexyl | —CH₃ |

A third embodiment of the novel compounds of this invention is that wherein $R^2$ and $R^3$ are independently $C_{1-3}$ alkyl or $C_{1-3}$ alkyl substituted with phenyl.

Specific compounds within this embodiment are those depicted in Table III.

TABLE III

| X | R¹ | R² | R³ | R⁴ |
|---|---|---|---|---|
| —(CH₂)₂— | 2,4-diClPh | —C₂H₅ | —C₂H₅ | —CH₃ |
| —(CH₂)₂— | 2,4-diClPh | —CH₃ | —CH₃ | benzyl |
| —(CH₂)₂— | cyclohexyl | —CH₃ | —CH₃ | benzyl |
| —(CH₂)₂— | 2,4-diClPh | —CH₃ | —CH₃ | —Ph |
| —CH₂— | cyclohexyl | —CH₃ | —CH₃ | —Ph |
| —(CH₂)₂— | 2,4-diClPh | —CH₃ | benzyl | —CH₃ |
| —(CH₂)₂— | cylcohexyl | —CH₃ | —CH₃ | i-propyl |
| —(CH₂)₂— | cyclohexyl | —C₂H₅ | —C₂H₅ | —CH₃ |
| —(CH₂)₄— | Ph | —C₂H₅ | —C₂H₅ | —CH₃ |
| —(CH₂)₂— | cyclohexyl | —CH₃ | —CH₃ | —CH₃ |
| —CH₂— | cyclohexyl | —C₂H₅ | —C₂H₅ | —CH₃ |
| —CH₂— | cyclohexyl | —CH₃ | —CH₃ | n-C₃H₇ |
| —(CH₂)₂— | 2,4-diClPh | —CH₃ | —CH₃ | i-propyl |
| —(CH₂)₂— | cyclohexyl | —CH₃ | —CH₃ | Ph |

A novel process for preparing the compounds of this invention is schematically exemplified below in Step (f). Steps (a) through (e) show how the penultimate intermediate can be synthesized and these steps are well known in the art and/or described in the Examples that follow.

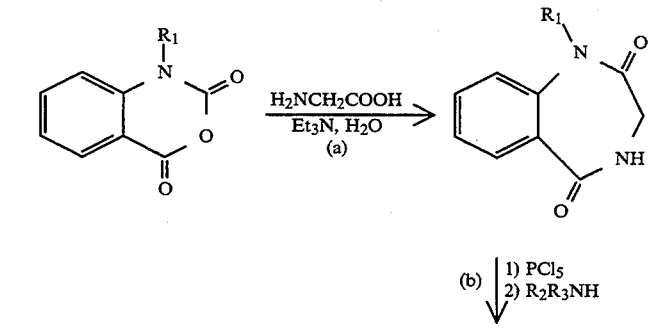

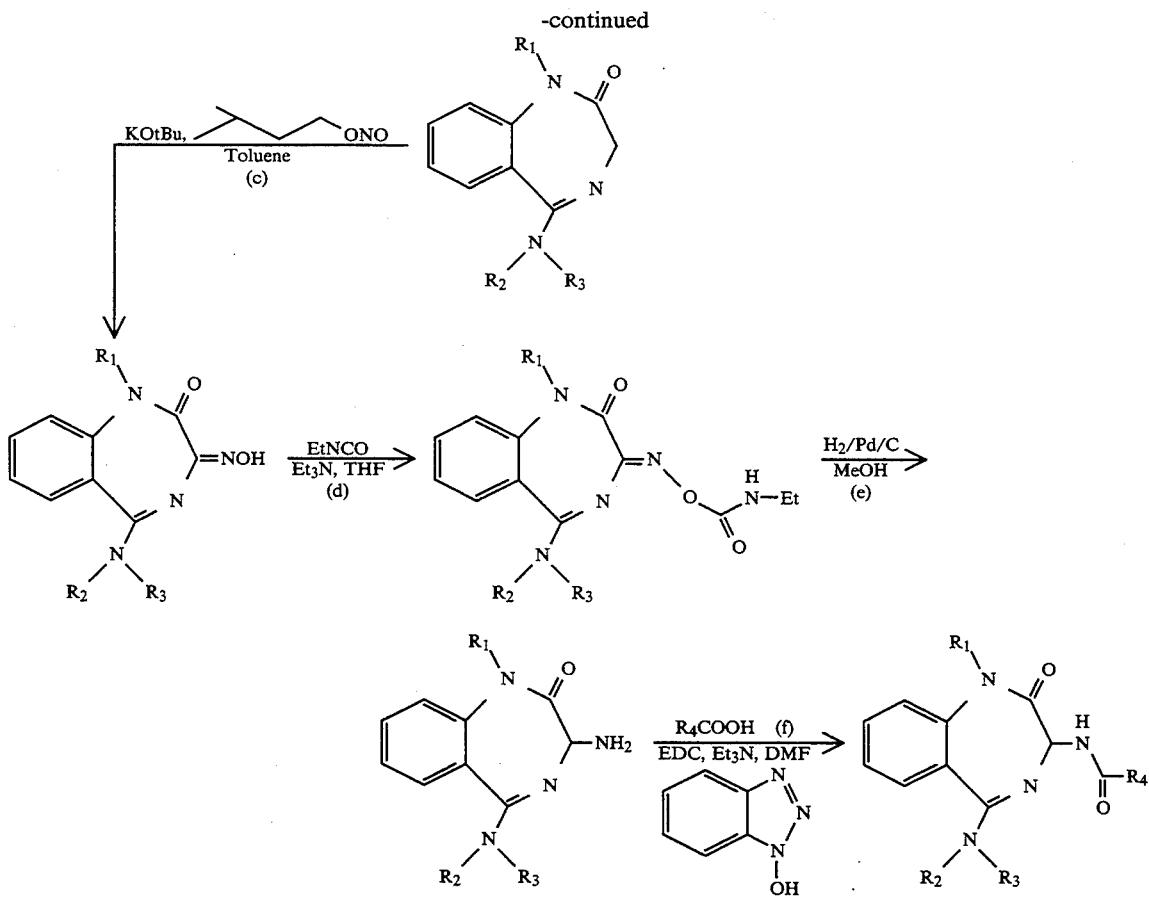

In the novel process, the 3-amino compound produced in Step (e) of the synthetic scheme is dissolved in a polar organic solvent such as DMF. The resulting solution is then treated with a carboxylic acid such as phenylpropionic acid depending on the nature of the 3-amide that is desired followed by treatment with 1-hydroxybenzotriazole hydrate, triethylamine and 1-(3-dimethyl-aminopropyl)-3-ethylcarbodiimide. When the reaction is complete after about 14–24 hours at about 15°–25° C., conveniently at-room temperature, it is poured into water and the product isolated by solvent extraction, evaporation and crystallization.

The novel compounds of the present invention, have the pharmacological properties required for antiarrhythmic agents of Class III, namely the prolongation of the myocardial action potential in vitro, without a significant depression of the Vmax, and the prolongation of QTc-interval in anesthetized dogs.

These compounds are effective in treating and preventing all types of arrhythmias including ventricular and atrial (supraventricular) arrhythmias. The compounds of the present invention are especially useful to control reentrant arrhythmias and prevent sudden death due to the ventricular fibrillation. These compounds are also effective in treating and preventing impaired cardiac pump functions.

In the novel method of this invention of treating arrhythmia, one of the compounds or pharmaceutically acceptable salt thereof, is administered in an amount ranging from about 0.0001 to about 20 mg per kg of body weight per day, preferably from about 0.001 to about 10 mg per kg of body weight per day in a single dose or in 2 to 4 divided doses.

These compounds can be administered as the sole active ingredient or in combination with other antiarrhythmic agents or other cardiovascular agents.

These compounds, or pharmaceutically acceptable salts thereof, in the described dosages, are administered orally, intraperitoneally, subcutaneously, intramuscularly, transdermally, sublingually or intravenously. They are preferably administered intravenously or orally, for example in the form of tablets, troches, capsules, elixirs, suspensions, syrups, wafers, chewing gum, or the like prepared by an recognized procedures. The amount of active compound in such therapeutically useful compositions or preparations is such that a suitable dosage will be obtained.

The activity of the compounds described herein as antiarrhythmic agents is measured by their ability to block the IKs and IKr as determined by the following test protocol.

Outward potassium currents are measured in single guinea pig ventricular myocytes using a whole-cell voltage clamp technique described in detail elsewhere (Sanguinetti and Jurkiewicz, 1990, two components of cardiac delayed actifier K+ current: differential sensitivity to block by Class III antiarrhythmic agents. J. Gen Physiol. 96:195–215). Myocytes are isolated by enzymatic (collagenase and protease) digestion of Langandorf perfused hearts. Single cells are then voltage clamped using 1 mm square-bore pipettes filled with 0.5M Kgluconate, 25 mM KCl, 5 mM K(2)ATP. Cells are bathed in a solution containing, in mN: 132 NaCl, 4 KCl, 1.2 MgCl[2], 10 HEPES, 10, glucose: pH 7.2, temp. 35° C.

Each cell is maintained at a holding potential of −50 mV. Test depolarizations are applied as voltage ramps from −85 to −50 mV, and as steps to −10 mV (0.5 s) and +50 mV (1.0 s). I[KI] is measured as peak outward current during the voltage ramp. I[Kr] is measured as tail currents upon repolarization from −10 mV to −50 mV. ILKS] is measured as time-dependent current during the pulse to +50 mV. Currents are measured during control, then after exposure to drug at two different concentrations.

Employing this test the compounds described herein have an $IC_{50}$ of less then 1000 nM as IKs and/or IKr blockers.

EXAMPLE 1

(±)-N-[2,3-dihydro-1-methyl-2-oxo-5-(N-cyclohexyl-N-methylamino)-1H-1,4-benzodiazepin-3-yl]-3-phenyl-propanamide Step A:

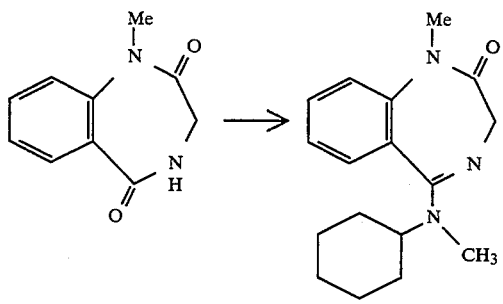

A solution of $PCl_5$ (6.6 g, 32 mmol) in 250 mL dichloromethane was added to a stirred solution of 1-methyl-1,4-benzodiazepine-2,5-dione (5.0 g, 26 mmol) in 150 mL of dichloromethane. The solution was stirred at room temperature for 3 hours before evaporation of volatiles. The resulting foam was dissolved in 200 mL dichloromethane, the solution cooled to 0° C. and a solution of N-methylcyclohexylamine (11.8 mL, 91 mmol) in 50 mL of dichloromethane added over 5 minutes. The reaction mixture was allowed to warm to room temperature, and partitioned. The organic phase was washed with brine, dried (MgSO4) and solvent evaporated to give the product as a foam. Yield 6.9 g.

NMR (300 MHz, CDCl3)δ:7.60 (m, 1H), 7.47–7.52 (m, 2H), 7.33 (m, 1H), 4.0 (½AB, J=12.2 Hz, 1H), 3.47 (½AB, J=12.2 Hz, 1H), 3.35 (s, 3H), 3.3 (m, 1H), 2.78 (s, 3H), 10–2.0 (m, 10H).

Step B:

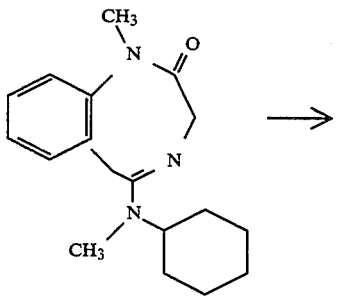

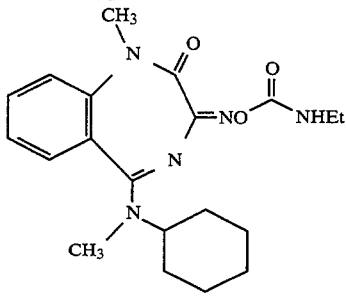

A solution of 2,3-dihydro-1-methyl-2-oxo-5-(N-cyclohexyl-N-methylamino)-1H-1,4-benzodiazepine (770 mg, 2.7 mmol) in 10 mL toluene was added to a stirred and cooled (30° C.) suspension of potassium t-butoxide (750 mg, 6.7 mmol) in 25 mL of toluene. After stirring at −30° C. for 30 minutes, isoamyl nitrite (540 μL, 4.0 mmol) was added and the reaction mixture stirred for 3 hours at −20° C. The mixture was then poured into 10% citric acid solution/ethyl acetate, stirred for 10 minutes, the pH adjusted to 7 with saturated potassium carbonate solution and the phases separated. The organic phase was washed with brine, the organic phase dried (MgSO4) and the solvent evaporated to give a foam. This was dissolved in 15 mL THF and ethyl isocyanate (395 μL, 5 mmol) added followed by triethylamine (700 μL, 5 mmol). The reaction mixture was heated to 60° C. for 2 hours, cooled to room temperature, the volatiles evaporated and the residue purified by flash column chromatography (silica, 75% ethyl acetate/hexane) to afford 720 mg of product as a foam.

NMR (300 MHz, CD3OD)δ: 7–7.6 (m, 5H), 3.5 (m, 1H), 3.42 (s, 3H), 2.7–3.3 (m, 5H), 1.1–2 (m, 10H), 1.05 (t, J=7 Hz, 3H).

Step C:

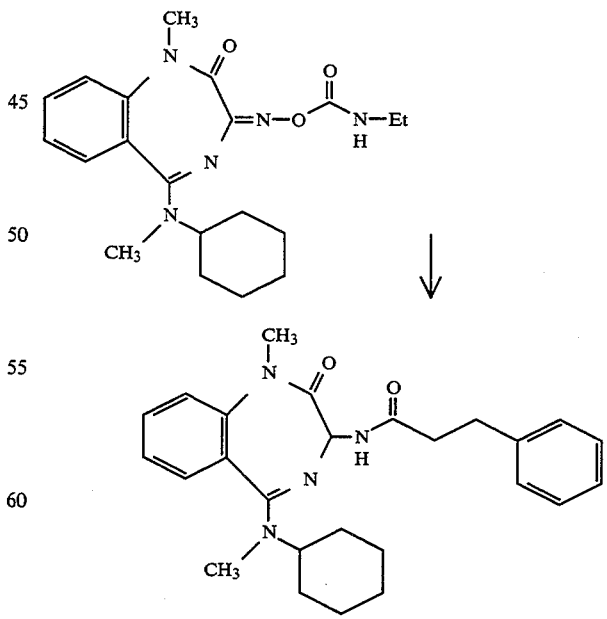

A solution of the oxime carbamate (355 mg, 1.85 mmol) in 30 mL methanol was hydrogenated at 50 psi over 300 mg of 10% palladium/charcoal for 3 hours.

The mixture was filtered through ceilte and the tiltrate evaporated to give the crude amine. This was dissolved in 5 ml DMF and phenylpropionic acid (300 mg, 2 mmol), 1-hydroxybenzotriazole hydrate (305 mg, 2 mmol), triethylamine (250 μL, 1.8 mmol) and 1-(3-dimethylaminopropyl)-3-ethylcarbodiimide (380 mg, 2 mmol) added. The reaction mixture was stirred at room temperature for 18 hours, poured into water and extracted with ethyl acetate. The organic phase was washed with sodium bicarbonate solution and brine, dried (MgSO$_4$) and solvent evaporated to give a solid, recrystallized from ethyl acetate/hexane to afford (±)-N-[2,3-Dihydro-1-methyl-2-oxo-5-(N-cyclohexyl-N-methylamino)-1H-1,4-benzo-diazepin-3-yl]-3-phenyl-propanamide.

m.p. 167°–168° C.

Anal. Calcd. for $C_{26}H_{32}N_4O_2 \cdot 0.75$ cyclohexane: C, 73.9; H, 8.34; N, 11.3. Found: C, 73.75; H, 8.36; N, 10.79%.

NMR (300 MHz, DMSO)δ:8.8 (d, J=7.5 Hz, 1H), 7.3–7.65 (m, 9H), 4.95 (d, J=7Hz, 1H), 3.57 (½AB, J=13 Hz, 1H), 3.48 (½AB, J=13 Hz, 1H), 3.1–3.4 (m, 1H), 3.27 (s, 3H), 2.65 (s, 3H), 0.9–1.9 (m, 10H).

By substituting the appropriate acid for phenylpropionic acid, and employing the procedures substantially as described in Example 1 the following compounds were prepared.

EXAMPLE 2

(±)-N-[2,3-Dihydro-1-methyl-2-oxo-5-(N-cyclohexyl-N-methylamino)-1H-1,4-benzo-diazepin-3-yl]-2-cyclohexylacetamide m.p. 158°–159° C. Anal. Calcd. for $C_{25}H_{36}N_4O_2$ 0.85 cyclohexane: C, 72.86; H, 9.39; N, 11.29. Found: C, 72.46; H, 9.4; N, 10.9%.

NMR (300 MHz, DMSO)δ: 8.44 (d, J=7.8 Hz, 1H), 7.5–7.65 (m, 2H), 7.46 (dd, J=7.8, 1.2 Hz, 1H), 7.32 (m, 1H), 4.95 (d, J=8 Hz, 1H), 3.15–3.45 (m, 1H), 3.26 (s, 3H), 2.64 (s, 3H), 1.95–2.1 (m, 2H), 0.8–1.9 (m, 21H).

EXAMPLE 3

N-[2,3-Dihydro-1-methyl-2-oxo-5-(N-cyclohexyl-N-methylamino)-1H-1,4-benzo-diazepin-3-yl]-4-phenyl-butanamide m.p. 140°–141° C. Anal. Calcd. for $C_{27}H_{34}N_4O_2$ 0.7 Water: C, 70.62; H, 7.77; N, 12.2. Found: C, 70.58; H, 7.54; N, 12.11%.

NMR (300 MHz, DMSO)δ:5:8.52 (d, J=8.1 Hz, 1H), 7.1–7.6 (m, 9H), 4.97 (d, J=9.1 Hz, 1H), 3.1–3.45 (m, 1H), 3.26 (s, 3H), 2.64 (s, 3H), 2.52 (m, 2H), 2.10–2.30 (m, 2H), 0.9–1.9 (m, 12H).

EXAMPLE 4

(±)-N-[2,3-Dihydro-1-methyl-2-oxo-5-(N-cyclohexyl-N-methylamino)-1H-1,4-benzo-diazepin-3,yl]-3-cyclohexylpropanamide m.p. 170°–171° C. Anal. Calcd. for $C_{26}H_{38}N_4O_2$ 0.55 EtOAc 0.5 cyclohexane: C, 70.81; H, 9.22; N, 10.59. Found: C, 70.88; H, 9.2; N, 10.55%.

NMR (300 MHz, DMSO)δ: 8.46 (d, J=8.1 Hz, 1H), 7.28–7.65 (m, 4H), 4.95 (d, J=8.1 Hz, 1H), 3.1–3.4 (m, 1H), 3.26 (s, 3H), 2.64 (s, 3H), 2.17 (t, J=7.1 Hz, 2H), 0.7–1.9 (m, 23H).

EXAMPLE 5

(±)-N-[2,3-Dihydro-1-methyl-2-oxo-5-(N-cyclohexyl-N-methylamino)-1H-1,4-benzo-diazepin-3-yl]-3-(4-trifluoromethyl)phenylpropanamide m.p. 221°–223 ° C. Anal. Calcd. for $C_{27}H_{31}F_3N_4O_2$: C, 64.79; H, 6.24; N, 11.19. Found: C, 64.73; H, 6.18; N, 11.07%.

NMR (300 MHz, DMSO)δ:8.63 (d, J=8.1 Hz, 1H), 7.25–7.65 (m, 8H), 4.96 (d, J=8 Hz, 1H), 3.15–3.45 (m, 1H), 3.26 (s, 3H), 2.84 (t, J=7.5 Hz, 2H), 2.63 (s, 3H), 2.53 (t, J=7.5 Hz, 2H), 0.9–1.9 (m, 10H).

EXAMPLE 6

(±)-N-[2,3-Dihydro-1-methyl-2-oxo-5-(N-cycohexyl-N-methylamino)-1H-1,4-benzo-diazepin-3,yl]-4-cyclohexylbutanamide m.p. 143°–145° C. Anal. Calcd. for $C_{27}H_{40}N_4O_2$, 1.0 $H_2O$: C, 68.9; H, 9; N, 11.9. Found: C, 68.85; H, 8.67; N, 12.01%.

NMR (300 MHz, DMSO)δ:8.46 (d, J=8.1 Hz, 1H), 7.25–7.65 (m, 4H), 4.95 (d, J=8 Hz, 1H), 3.15–3.4 (m, 1H), 3.26 (s, 3H), 2.64 (s, 3H), 2.13 (d, J=7.5 Hz, 2H), 0.7–1.9 (m, 25H).

EXAMPLE 7

(±)-N-[2,3-Dihydro-1-methyl-2-oxo-5-(N-cyclohexyl-N-methylamino)-1H-1,4-benzo-diazepin-3-yl]-3-(2,4-dichlorophenyl)-propanamide m.p. 184°–185 ° C. Anal. Calcd. for $C_{26}H_{30}Cl_2N_4O_2$, 0.8 $H_2O$: C, 60.53; H, 6.17; N, 10.86. Found: C, 60.5; H, 5.61; N, 10.82%.

NMR (300 MHz, DMSO)δ:8.66 (d, J=8.1 Hz, 1H), 7.2–7.65 (m, 7H), 4.96 (d, J=8.1 Hz, 1H), 3.15–3.4 (m, 1H), 3.26 (s, 3H), 2.83 (d, J=7.2 Hz, 2H), 2.64 (s, 3H), 2.5 (t, 2H), 0.9–1.9 (m, 10H).

By using diethylamine in place of N-methylcyclohexylamine and the appropriate acid, the following compounds were prepared by the processes described in Example 1.

EXAMPLE 8

(±)-N-[2,3-Dihydro-1-methyl-2-oxo-5-(N,N-diethylamino)-1H-1,4-benzodiazepin,3-yl]-3-(2,4-dichlorophenyl)propanamide m.p. 177°–178° C. Anal. Calcd. for $C_{23}H_{26}Cl_2N_4O_2$: C, 59.87; H, 5.68; N, 12.14. Found: C. 60.2; H, 5.63; N, 11.91%.

NMR (300 MHz, DMSO)δ:8.64 (d, J=8.1 Hz, 1H), 7.2–7.6 (m, 7H), 4.97 (d, J=8.1 Hz, 1H), 3.25–3.4 (m, 2H), 3.27 (s, 3H), 2.9–3.1 (m, 2H), 2.83 (t, J=7.3 Hz, 2H), 2.5 (t, 2H), 0.98 (t, J=6.9 Hz, 6H).

EXAMPLE 9

(±)-N-[2,3-Dihydro-1-methyl-2-oxo-5-(N,N-diethylamino)-1H-1,4-benzodiazepin-3-yl]-5-phenylpentanamide m.p. 134°–135° C. Anal. Calcd. for $C_{25}H_{32}N_4O_2$, 0.25 $H_2O$: C, 70.64; H, 7.71; N, 13.18. Found: C, 70.7; H, 7.94; N, 13.16%.

NMR (300 MHz, DMSO)δ: 8.48 (d, J=8.1 Hz, 1H), 7.1–7.6 (m, 9H), 4.97 (d, J=8.1 Hz, 1H), 3.25–3.4 (m, 2H), 3.27 (s, 3H), 2.95–3.1 (m, 2H), 2.53 (t, J=7.1 Hz, 2H), 2.20 (t, J=7.1 Hz, 2H), 1.4–1.6 (m, 4H), 0.97 (t, J=7.1 Hz, 6H).

EXAMPLE 10

(±)-N-[2,3-Dihydro-1-methyl-2-oxo-5-(N,N-diethylamino)-1H-1,4-benzodiazepin-3-yl]-2-cyclohexylacetamide m.p. 192°–193° C. Anal. Calcd. for $C_{22}H_{32}N_4O_2$, 0.9 $H_2O$: C, 65.93; H, 8.5; N, 13.98. Found: C, 65.91; H, 7.9; N, 14.05%.

NMR (300 MHz, DMSO)δ: 8.43 (d, J=8.1 Hz, 1H), 7.2–7.65 (m, 4H), 4.96 (d, J=8.1 Hz, 1H), 3.2–3.3 (m, 2H), 3.27 (s, 3H), 2.9–3.1 (m, 2H), 1.95–2.1 (m, 2H), 0.8–1.7 (m, 17H).

EXAMPLE 11

(±)-N-[2,3-Dihydro-1-methyl-2-oxo-5-(N,N-diethylamino)-1H-1,4-benzodiazepin-3-yl]-3-cyclohexylpropanamide m.p. 209°–210° C. Anal. Calcd. for $C_{23}H_{34}N_4O_2$: C, 69.31; H, 8.6; N, 14.06. Found: C, 69.38; H, 8.69; N, 13.69%.

NMR (300 MHz, DMSO)δ:8.45 (d, J=8.1 Hz, 1H), 7.2–7.65 (m, 4H), 4.96 (d, J=8.1 Hz, 1H), 3.2–3.4 (m, 2H), 3.27 (s, 3H), 2.9–3.1 (m, 2H), 2.17 (t, J=7.3 Hz, 2H), 0.7–1.7 (m, 19H).

By using hexahydroazepine in place of N-methylcyclohexylamine, and the appropriate acid the following compounds were prepared using the processes substantially as described in Example 1.

EXAMPLE 12

N-[2,3-Dihydro-1-methyl-2-oxo-5-(hexahydroazepin-1-yl)-1H-1,4-benzodiazepin-3-yl]-4-phenylbutanamide m.p. 182°–183° C. Anal. Calcd. for $C_{26}H_{32}N_4O_2$ C, 72.19; H, 7.46; N, 12.95. Found: C, 71.79; H, 7.36; N, 12.57%.

NMR (300 MHz, $CD_3OD$)δ: 1.20–1.98 (m, 10H), 2.27 (m, 2H), 2.62 (m, 2H), 3.41 (m, 4H), 4.94 (s, 3H), 5.09 (d, 1H), 7.10–7.62 (m, 9H).

EXAMPLE 13

N-[2,3-Dihydro-1-methyl-2-oxo-5-(hexahydroazepin-1-yl)-1H-1,4-benzodiazepin-3-yl]-2-cyclohexy acetamide m.p. 205°–207° C. Anal. Calcd. for $C_{24}H_{34}N_4O_2.0.25\ H_2O$ C, 70.21; H, 8.35; N, 13.65. Found: C, 69.44; H, 8.38; N, 13.50%.

NMR (300 MHz, $CD_3OD$)δ0.95–2.83 (m, 19H), 2.08 (m, 2H), 3.41 (m, 4H), 4.94 (s, 3H), 5.09 (d, 1H), 7.29–7.63 (m, 4H).

EXAMPLE 14

(±)-3-(2,4-Dichlorophenyl)-N-[2,3-dihydro-1-methyl-2-oxo-5-(hexahydroazepin-1-yl)-1H-1,4-benodiazepin-3-yl]propanamide m.p. 155°–157° C. Anal. Calcd. for $C_{25}H_{28}C_{12}N_4O_2.HCl$, 0.12 EtOAc: C, 57.26; H, 5.65; N, 10.48. Found: C, 57.66; H, 5.75; N, 10.08%.

NMR δ: 8.66 (d, J=9.0 Hz, 1H), 7.80–7.74 (m, 1H), 7.56–7.41 (m, 3H), 7.32–7.23 (m, 2H), 7.14 (dd, J=8.3, 2.2 Hz, 1H), 5.68 (m, 1H), 4.27–4.00 (m, 2H), 3.58–3.5 (m, 2H), 3.46 (s, 3H), 3.07 (t, J=7.6 Hz, 2H), 2.86–2.77 (m, 2H), 2.18–1.99 (m, 2H), 1.86–1.56 (m, 6H).

EXAMPLE 15

(±)-3-cyclohexyl-N-[2,3-Dihydro-1-methyl-2-oxo-5-(hexahydroazepin-1yl)-1H 1,4-benzodiazepin-3-yl]propanamide m.p. 100°–102° C. Anal. Calcd. for $C_{25}H_{36}N_4O_2.HCl$, 0.50 $H_2O$; 0.30 EtOAc: C, 63.38; H, 8.2; N, 11.28. Found: C, 63.36; H,8.09; N, 11.3%.

δ:8.54 (d, J=9.0 Hz, 1H), 7.79–7.74 (m, 1H), 7.54 (d, J=7.8 Hz, 1H), 7.49–7.40 (m, 2H), 5.69 (dd, J=9.0, 5.6 Hz, 2H), 4.55–4.4 (m, 1H), 4.20–4.00 (m, 1H), 3.54–3.49 (m, 2H), 3.46 (s, 3H), 2.47–2.41 (m, 2H), 2.09–1.97 (m, 5H), 1.82–1.51 (m, 1 OH), 1.28–1.12 (m, 4H), 0.93–0.85 (m, 2H).

EXAMPLE 16

(±)-N-[2,3-Dihydro-1-methyl-2-oxo-5-(hexahydroazepin-1-yl)-1H-1,4-benzodiazepin-3-yl]-4-cyclohexylbutanamide m.p. 186.5°–187.5° C. Anal. Calcd. for $C_{26}H_{38}N_4O_2$: C, 71.2; H, 8.73; N, 12.77. Found: C, 70.15; H, 8.45; N, 12.32%.

δH($CD_3OD$): 0.90 (m, 2H), 1.23 (m, 8H), 1.42–1.88 (m, 13H), 3.38 (m, 7H), 5.10 (s, 1H), 7.31–7.63 (m, 4H).

EXAMPLE 17

(±)-N-[2,3-Dihydro-1-methyl-2-oxo-5-(hexahydroazepin-1-yl)-1H-1,4-benzodiazepin-3-yl]-5-phenylpentanamide m.p. 140°–141° C. δH($CD_3OD$) 1.66 (m, 12H), 2.36 (m, 2H), 2.66 (m, 2H), 3.38 (m, 7H), 5.10 (s, 1H), 7.20–7.56 (m, 9H). Anal. Calcd. for $C_{27}H_{34}N_4O_2$ with 0.25 water: C, 72.62; H, 7.67; N, 12.55. Found: C, 71.88; H, 7.71; N, 12.42%.

EXAMPLE 18

(±)-N-[2,3-Dihydro-1-methyl-2-oxo-5-(hexahydroazepin-1-yl)-1H-1,4-benzodiazepin-3-yl]-3-[4-trifluoromethylphenyl]propanamide m.p. 169°–170° C. Anal. Calcd. for $C_{26}H_{29}N_4O_2F_3$: C, 64.18; H, 6.01; N, 11.52. Found: C, 63.01; H, 5.77; N, 11.21%.

δH($CD_3OD$) 1.60 (m, 8H), 2.65 (m, 2H), 2.99 (t, 2H), 3.39 (m, 7H), 5.10 (s, 1H), 7.31–7.62 (m, 8H).

By using N-methylbenzylamine in place of N-methylcyclohexylamine, and the appropriate acid, the following compound was prepared using the processes substantially as described in Example 1.

EXAMPLE 19

(±)-N-[2,3-Dihydro-1-methyl-2-oxo-5-(N-benzyl-N-methylamino)-1H-1,4-benzodiazepin-3-yl]-3-[2,4-dichlorophenyl]propanamide m.p. 169°–170° C.

δH(DMSO) 0.80 (m, 2H), 1.09 (m, 7H), 1.36 (m, 5H), 1.62 (m, 5H), 2.16 (t, 2H), 2.78 (s, 6H), 4.40 (m, 1H), 4.90 (d, 1H), 7.33–7.62 (m, 4H), 8.41 (d, 1H).

By using dimethylamine in place of N-methylcyclohexylamine and the appropriate acid, the following compound was prepared using the process substantially as described in Example 1.

EXAMPLE 20

(±)-N-[2,3-Dihydro-1-methyl-2-oxo-5-(N,N-dimethylamino)-1H-1,4-benzodiazepin-3-yl-3-cyclohexylpropanamide m.p. 197.5°–198° C. Anal. Calcd. for $C_{21}H_{30}N_4O_2 \cdot 0.05$ C, 68.08; H, 8.16; N, 15.12. Found: C, 67.91; H, 8.17; N, 14.95%.

NMR (300 MHz, $CDCl_3$)δ0.81–1.77 (m, 13H), 2.30 (m, 2H), 2.86 (s, 6H), 3.21 (s, 3H), 5.26 (d, 1H), 6.99 (d, 1H), 7.22–7.52 (m, 4H)

2,3-Dihydro-1-benzyl-2-oxo-1H-1,4-benzodiazepine-2,5-dione was prepared from N-benzylisatoic anhydride (Transworld Chemicals) and glycine using the method described by Bock et al *J. Org. Chem.* 52, 1644, (1987). This was then reacted with dimethylamine in place of the N-methylcyclohexylamine, and the appropriate acid substantially as described above in Example 1 to give the following compounds:

EXAMPLE 21

(±)-N-[2,3-Dihydro-1-benzyl-2-oxo-5-(N,N-dimethylamino)-1H-1,4-benzodiazepin-3-yl]-3-[2,4-dichlorophenyl]-propanamide m.p. 193°–194° C. Anal. Calcd. for $C_{27}H_{26}Cl_2N_4O_2$: C, 63.66; H, 5.14; N, 11. Found: C, 63.73; H, 5.11; N, 11.16%.

δH(DMSO) 2.53 (m, 2H), 2.86 (t, 2H), [(3.31, s), (3.34, s) 6H], 4.80 (d, 1H), 5.05 (m, 1H), 5.49 (d, 1H), 6.94–7.72 (m, 12H), 8.79 (d, 1H).

EXAMPLE 22

(±)-N-[2,3-Dihydro-1-benzyl-2-oxo-5-(N,N-dimethylamino)-1H-1,4-benzodiazepin-3-yl]-3-cyclohexylpropanamide m.p. 136°–137° C. Anal. Calcd. for $C_{27}H_{34}N_4O_2$: C, 72.62; H, 7.67; N, 12.55. Found: C, 72.35; H, 7.56; N, 12.62%.

δH($CD_3OD$) 0.84–1.82 (m, 13H), 2.35 (m, 2H), 2.68 (s, 6H), 4.74 (d, 1H), 5.16 (s, 1H), 5.65 (d, 1H), 7.04–7.67 (m, 9H).

2,3-Dihydro-1-isopropyl-2-oxo-1H-1,4-benzodiazepine-2,5-dione was prepared from N-isopropylisatoic anhydride and glycine using the method described by Bock, et at., *J. Org. Chem.* 52, 1644, (1987). This was then reacted with dimethylamine in place of the N-methyl cyclohexylamine, and the appropriate acid substantially as described in Example 1 to give the following compounds:

EXAMPLE 23

(±)-N-[2,3-dihydro-1-isopropyl-2-oxo-5-(N,N-dimethylamino)-1H-1,4-benzodiazepin-3-yl]-3-cyclohexylpropanamide m.p. 209°–210° C. Anal. Calcd. for $C_{23}H_{34}N_4O_2$ with 0.95 $H_2O$: C, 66.45; H, 8.71; N, 13.48. Found: C, 66.38; H, 8.23; N, 13.5%.

EXAMPLE 24

(±)-N-[2,3-Dihydro-1-isopropyl-2-oxo-5-(N,N-dimethylamino)-1H-1,4-benzodiazepin-3-yl]-3,[2,4-dichlorophenyl]propanamide m.p. 219°–220° C. Anal. Calcd. for $C_{23}H_{26}Cl_2N_4O_2$). 0.9 $H_2O$: C, 57.84; H, 5.87; N, 11.73. Found: C, 57.83; H, 5.50; N, 11.72%.

NMR (300 MHz, DMSO)δ1.09 (d, 3H), 1.36 (d, 3H), 2.49 (m, 2H), 2.80 (m, 8H), 4.40 (m, 1H), 4.90 (d, 1H), 7.28–7.61 (m, 7H), 8.62 (d, 1H).

2,3-Dihydro-1-phenyl-2-oxo-1H-1,4-benzodiazepin-2,5-dione (Japanese Patent 21,617) was carded forward as described above using dimethylamine in place of N-methylcyclohexylamine and the appropriate carboxylic acid to give the compounds of Examples 25 and 26.

EXAMPLE 25

(±)-N-[2,3-Dihydro-1-phenyl-2-oxo-5-(N,N-dimethylamino)-1H-1,4-benzodiazepin-3-yl]-2-cyclohexylacetamide m.p. 264°–266° C. Anal. Calcd. for $C_{25}H_{30}N_4O_2$, 0.2 $H_2O$: C, 71.12; H, 7.26; N, 13.27. Found: C, 71.12; H, 7.15; N, 13.29%.

NMR (300 MHz, DMSO)δ8.57 (d, J=8.1 Hz, 1H), 7.54 (dd, J=7.8, 0.6 Hz, 1H), 7.1–7.5 (m, 7H), 6.92 (d, J=8.1 Hz, 1H), 5.15 (d, J=7.6 Hz, 1H), 2.88 (s, 6H), 2.07 (d, J=6.8 Hz, 2H), 0.8–1.8 (m, 11 H).

EXAMPLE 26

(±)-N-[2,3-Dihydro-1-phenyl-2-oxo-5-(N,N-dimethylamino)-1H-1,4-benzodiazepin-3-yl]-3-(2,4-dichlorophenyl)propanamide m.p. 259°–260° C. Anal. Calcd. for $C_{26}H_{24}C_{12}N_4O_2$: C, 62.86; H, 4.81; N, 11.35. Found: C, 63.04; H, 4.88; N, 11.31%.

NMR (300 Hz, DMSO)δ: 8.79 (d, J=7.8 Hz, 1H), 7.1–7.6 (m, 7H), 6.91 (dd, J=8.4, 0.9 Hz, 1H), 5.17 (d, J=7.8 Hz, 1H), 2.9 (s, 6H), 2.85 (t, 2H), 2.55 (t, 2H).

2,3-Dihydro-1-propyl-2-oxo-1H-1,4-benzodiazepin-2,5-dione was carried forward as described above using dimethylamine or N-methylcyclohexylamine and the appropriate carboxylic acid to give the compounds of Examples 27–30.

EXAMPLE 27

(±)-N-[2,3-Dihydro-1-propyl-2-oxo-5-(N-cyclohexyl-N-methylamino)-1H-1,4-benzo-diazepin-3-yl-3-cyclohexylpropionamide m.p. 144°–145° C. Anal. Calcd. for $C_{28}H_{42}N_4O_2$, 0.25 $H_2O$: C, 71.37; H, 9.09: N, 11.89. Found: C, 71.4; H, 8.95; N, 11.82%.

NMR (300 MHz, DMSO) d: 8.43 (d, J=7.8 Hz, 1H), 7.25–7.6 (m, 4H), 4.92 (d, J=8.1 Hz, 1H), 4.2 (m, 1H), 3.55 (m, 1H), 2.64 (s, 3H), 2.16 (brt, 2H), 0.7–1.9 (m, 25H), 0.65 (t, J=7.3 Hz, 3H).

EXAMPLE 28

(±)-N-[2,3-Dihydro-1-propyl-2-oxo-5-(N-cyclohexyl-N-methylamino)-1H-1,4-benzo-diazepin-3-yl]-2-cyclohexylacetamide m.p. 137°–140° C. Anal. Calcd. for $C_{27}H_{40}N_4O_2$, 1.0 $H_2O$: C, 68.9; H, 9; N, 11.9. Found: C, 68.8; H, 8.93; N, 11.98%.

NMR (300 MHz, DMSO) δ:8.43 (d, J=7.8 Hz, 1H), 7.25–7.65 (m, 4H), 4.92 (d, J=8 Hz, 1H), 4.22 (m, 1H), 3.58 (m, 1H), 2.65 (s, 3H), 0.8–2.15 (m, 25H), 0.65 (t, 3H).

EXAMPLE 29

(±)-N-[2,3-Dihydro-1-propyl-2-oxo-5-(N-cyclohexyl-N-methylamino)-1H-1,4-benzo-diazepin-3-yl]-3-(2,4-dichlorophenyl)propionamide m.p. 167°–169° C. Anal. Calcd. for $C_{28}H_{34}C_{12}N_4O_2$: C, 63.51; H, 6.47; N, 10.58. Found: C, 63.44; H, 6.44; N, 10.46%.

NMR (300 MHz, DMSO) δ:8.66 (d, J=8.3 Hz, 1H), 7.2–7.65 (m, 7H), 4.93 (d, J=8.1 Hz, 1H), 4.20 (m, 1H), 3.60 (m, 1H), 2.8 (t, J=7.3 Hz, 2H), 2.64 (s, 3H), 2.5 (t, 2H), 0.8–1.9 (m, 12H), 0.65 (t, J=7.3 Hz, 3H).

EXAMPLE 30

(±)-N-[2,3-Dihydro-1-propyl-2-oxo-5-(N,N-dimethylamino)-1H-1,4-benzodiazepin-3-yl]-2-cyclohexylacetamide m.p. 196°–197° C. Anal. Calcd. for $C_{22}H_{32}N_4O_2$: C, 68.72; H, 8.39; N, 14.57. Found: C, 68.54; H, 8.31; N, 14.44%.

NMR (300 MHz, DMSO) δ:0.59–2.12 (m, 16H), 2.78 (m, 2H), 3.32 (5, 6H), 3.58 (m, 1H), 4.19 (m, 1H), 4.95 (d, 1H), 7.30–7.62 (m, 4H), 8.46 (d, 1H).

What is claimed is:

1. A compound of structural formula:

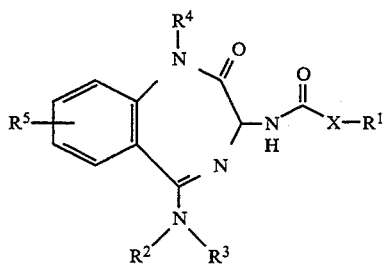

individual diastereomers, enantiomers and mixtures thereof or a pharmaceutically acceptable salt thereof wherein:

X is $C_{1-4}$ alkylene, either straight or branched chain.

$R^1$ is
1) phenyl either unsubstituted or substituted with one or two substituents selected from chloro, bromo, iodo, fluoro, trifluoromethyl $C_{1-3}$ alkoxy or nitro;
2) naphthyl, or
3) $C_{5-7}$ cycloalkyl, $R^2$ and $R^3$ are independently
1) $C_{1-3}$ alkyl, either straight or branched chain, and either unsubstituted or substituted with phenyl, or
2) $C_{3-7}$ cycloalkyl; or $R^2$ and $R^3$ taken together represent a $C_{4-7}$ methylene chain to form with the nitrogen to which they are attached a 5–8 membered azacycle;

$R^4$ is
1) $C_{1-4}$ alkyl,
2) phenyl or
3) benzyl; and $R^5$ is
1) hydrogen or
2) $C_{1-3}$ alkyl.

2. The compound of claim 1, wherein $R^2$ and $R^3$ are joined together to form with the nitrogen to which they are attached a 5–8 membered azacycle.

3. The compound of claim 2 selected from the group consisting of these depicted in the following table:

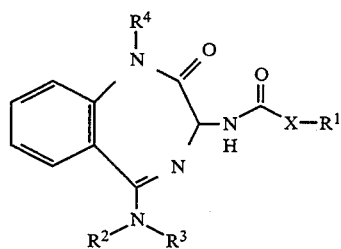

| X | $R^1$ | $R^2$–$R^3$ | $R^4$ |
|---|---|---|---|
| —CH₂— | 1-naphthyl | —(CH₂)₅— | n-propyl |
| —(CH₂)₂— | 2,4-diClPh | —(CH₂)₆— | methyl |
| —(CH₂)₂— | 4-CF₃Ph | —(CH₂)₆— | methyl |
| —(CH₂)₃— | cyclohexyl | —(CH₂)₆— | methyl |
| —(CH₂)₄— | Ph | —(CH₂)₆— | methyl |
| —CH₂— | 1-naphthyl | —(CH₂)₆— | n-propyl |
| —(CH₂)₃— | Ph | —(CH₂)₆— | methyl |
| —(CH₂)₂— | cyclohexyl | —(CH₂)₆— | methyl |
| —CH₂— | cyclohexyl | —(CH₂)₆— | methyl. |

4. The compound of claim 1, wherein $R^2$ and $R^3$ are independently $C_{1-3}$ alkyl or $C_{5-7}$ cycloalkyl.

5. The compound of claim 4 selected from the group consisting of those depicted in the following table:

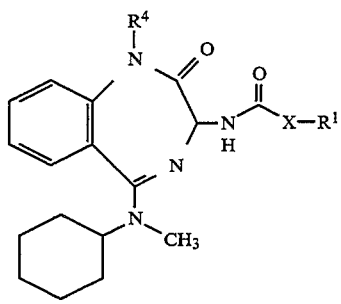

| X | $R^1$ | $R^4$ |
|---|---|---|
| —(CH₂)₂— | 4-CF₃Ph | —CH₃ |
| —(CH₂)₃— | cyclohexyl | —CH₃ |
| —(CH₂)₂— | 2,4-diClPh | —CH₃ |
| —(CH₂)₂— | 2,4-diClPh | n-propyl |
| —(CH₂)₂— | cyclohexyl | n-propyl |
| —CH₂— | cyclohexyl | n-propyl |
| —(CH₂)₂— | Ph | —CH₃ |
| —CH₂— | cyclohexyl | —CH₃ |
| —(CH₂)₃— | Ph | —CH₃ |
| —(CH₂)₂— | cyclohexyl | —CH₃. |

6. The compound of claim 1 wherein $R^2$ and $R^3$ are independently $C_{1-3}$ alkyl or $C_{1-3}$ alkyl substituted with phenyl.

7. The compound of claim 6 selected from the group consisting of those depicted in the following table:

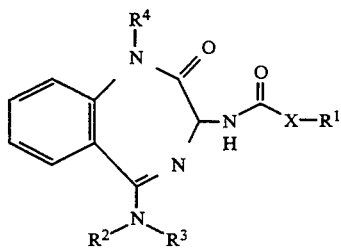

| X | R¹ | R² | R³ | R⁴ |
|---|---|---|---|---|
| —(CH₂)₂— | 2,4-diClPh | —C₂H₅ | —C₂H₅ | —CH₃ |
| —(CH₂)₂— | 2,4-diClPh | —CH₃ | —CH₃ | benzyl |
| —(CH₂)₂— | cyclohexyl | —CH₃ | —CH₃ | benzyl |
| —(CH₂)₂— | 2,4-diClPh | —CH₃ | —CH₃ | —Ph |
| —CH₂— | cyclohexyl | —CH₃ | —CH₃ | —Ph |
| —(CH₂)₂— | 2,4-diClPh | —CH₃ | benzyl | —CH₃ |
| —(CH₂)₂— | cylcohexyl | —CH₃ | —CH₃ | i-propyl |
| —(CH₂)₂— | cyclohexyl | —C₂H₅ | —C₂H₅ | —CH₃ |
| —(CH₂)₄— | Ph | —C₂H₅ | —C₂H₅ | —CH₃ |
| —(CH₂)₂— | cyclohexyl | —CH₃ | —CH₃ | —CH₃ |
| —CH₂— | cyclohexyl | —C₂H₅ | —C₂H₅ | —CH₃ |
| —CH₂— | cyclohexyl | —CH₃ | —CH₃ | n-C₃H₇ |
| —(CH₂)₂— | 2,4-diClPh | —CH₃ | —CH₃ | i-propyl |
| —(CH₂)₂— | cyclohexyl | —CH₃ | —CH₃ | Ph. |

\* \* \* \* \*